United States Patent [19]
Metz

[11] Patent Number: 5,423,784
[45] Date of Patent: Jun. 13, 1995

[54] EXTENDED MALE CATHETER APPLICATOR AND METHODS OF USE

[75] Inventor: Michael Metz, Chicago, Ill.

[73] Assignee: Hollister Incorporated, Libertyville, Ill.

[21] Appl. No.: 264,190

[22] Filed: Jun. 22, 1994

Related U.S. Application Data

[63] Continuation of Ser. No. 180,101, Jan. 11, 1994, abandoned.

[51] Int. Cl.$^6$ ............................................. A61F 5/44
[52] U.S. Cl. ................................. 604/351; 604/349; 128/844
[58] Field of Search ............................ 604/349–353, 604/343, 345; 128/844

[56] References Cited

U.S. PATENT DOCUMENTS

| 934,382 | 6/1990 | Barone, Jr. | 128/844 |
| 3,421,507 | 1/1969 | Gresham | 604/349 |
| 3,835,857 | 2/1973 | Rogers et al. | 128/295 |
| 3,863,638 | 2/1975 | Rogers et al. | 128/295 |
| 4,187,851 | 2/1980 | Hauser | 128/295 |
| 4,378,018 | 3/1983 | Alexander et al. | 128/295 |
| 4,540,409 | 9/1985 | Nystrom | 604/349 |
| 4,581,026 | 4/1986 | Schneider | 604/352 |
| 4,626,250 | 12/1986 | Schneider | 604/352 |
| 4,840,187 | 6/1989 | Brazier | 128/844 |
| 5,070,890 | 12/1991 | Papurt | 128/844 |
| 5,267,990 | 12/1993 | Cross et al. | 604/349 |
| 5,275,587 | 1/1994 | Kubalak et al. | 604/349 |
| 5,336,211 | 8/1994 | Metz | 604/352 |

FOREIGN PATENT DOCUMENTS 0325902 2/1989 European Pat. Off. .
2120102 11/1988 United Kingdom .

Primary Examiner—Jerome L. Kruter
Attorney, Agent, or Firm—Tilton Fallon Lungmus

[57] ABSTRACT

The combination of an external male catheter and an applicator to facilitate properly fitting the catheter on a patient, as well as the methods of use and making, are disclosed. The catheter is preferably of the type disclosed in U.S. Pat. 4,540,409 and the applicator takes the form of a relatively rigid open-ended tube and a flexible, torous-shaped sleeve that continuously and rotatably surrounds the wall of the tube and slides easily against the outer and inner surfaces of the tube. A user applies the catheter by gripping and pulling the exposed outlet section of the catheter to extract the catheter from one end of the applicator tube while the interior surfaces of the catheter sheath at the opposite end of the applicator tube are in contact with the penis.

16 Claims, 4 Drawing Sheets

EXTENDED MALE CATHETER APPLICATOR AND METHODS OF USE

This is a continuation of application Ser. No. 180,101, filed on Jan. 11, 1994, now abandoned.

BACKGROUND

The use of external catheters for male urinary drainage systems is well known, as disclosed in U.S. Pat. Nos. 4,378,018, 4,187,851, 3,863,638 and 3,835,857. Essentially, such a system comprises an elastic sheath adapted to fit over the user's penis, the sheath having an outlet at its distal end connected to a tube leading to a suitable collection receptacle. The sheath includes a cylindrical body portion that fits over the penile shaft, a tapered neck portion that functions as a surge chamber near the distal end of the sheath, and a reduced drainage tube portion that extends beyond the neck portion. In a preferred construction, the sheath also includes an inner sleeve portion for sealingly (but non-adhesively) engaging the head or glans of the penis as disclosed in U.S. Pat. Nos. 4,581,026 and 4,626,250.

External catheters also quite commonly have an annular layer of pressure-sensitive adhesive on the inner surfaces of their cylindrical portions to retain the sheaths in place. Whether adhesive-coated or not, such catheters are usually marketed in rolled form with instructions that the sheaths be unrolled during application in essentially the same manner as a prophylactic condom.

Experience has revealed that such an application procedure is more difficult than it sounds. Orienting and unrolling a sheath with respect to a flaccid (and possibly retracted) penis is difficult even for a patient that retains manual dexterity and is capable of applying such a product to himself; it is obviously more difficult for a nurse or other attendant who lacks the tactile feedback that would assist a patient in carrying out the procedure on himself. The problems are compounded by the fact that a nurse undertaking such a procedure would normally wear surgical gloves and, should such gloves happen to contact the adhesive of the catheter as it is being unrolled, the gloves and catheter may adhere strongly to each other. Experience indicates that problems of applying such a catheter tend to be reduced if a nurse holds the penis in one hand and directs it into the opening of the rolled catheter held in the other, and then, immediately after commencing the unrolling operation, externally grips the sheath-covered glans and stretches or extends the penis as the unrolling operation is continued. It is believed, however, that nurses sometimes fail to perform such procedures completely, or with sufficient patience and care, because they are concerned about possible discomfort or injury to the patient, or are rushing to perform other healthcare duties, or simply because they find themselves uncomfortable making such direct and extended contact with the limp penis of an incontinent patient. Often the result is that such an external catheter is improperly or incompletely applied, causing discomfort and resulting in leakage of urine when the drainage system is in use.

Other systems have been proposed in the past that utilize non-rolled sheaths and would not present the unrolling problems described above. Co-owned U.S. Pat. No. 4,540,409 discloses a catheter which has its cylindrical portion externally supported by a rigid and slightly tapered applicator tube. The neck and drainage tube portions of the catheter are reverted and extend through the interior of the tube. In applying the catheter, the entrance opening of the tube is directed towards the glans and the user grips the outlet tube section of the catheter to restrain that section, or even exerts a gentle pulling force, while at the same time urging the applicator tube in the direction of the penis. It has been found, however, that static friction between the applicator tube and the portion of the catheter stretched about it is not easily broken. Pushing the applicator tube more forcefully against the patient in order to overcome such frictional resistance may not only cause discomfort and possible injury to the patient but is unlikely to be effective because of the flaccidity of the target. Applying pulling force to the outlet tube portion of the catheter in an effort to break such static friction tends to have an opposite effect; the catheter simply stretches more tightly into engagement with the surfaces of the applicator tube at and about its entrance opening.

U.S. Pat. No. 4,840,187 discloses a sheath and applicator tube combination in which a liner casing of netting material is interposed between the tube and sheath to reduce static and sliding friction. The applicator tube is closed at one end and the netting is internally secured to the tube at that end. Inversion of the sheath is produced by pushing the sheath-covered open end of the applicator tube against the glans, although side window openings in the applicator tube do allow the user to grip and guide the distal portion of the penis (and the sheath liner casing covering it) into the interior of the tube.

British patent GB 2,120,102B discloses a more complex device in which an applicator tube is provided with a slideable internal tube 14 and a slideable external ring 15 connected to opposite ends of a woven liner. Use of the device is described as requiring the user to steady the penis with one hand while at the same time pulling draw pin 16 axially to shift the inner sliding tube 14 within support tube 11 to evert both the woven liner and the sheath carried by it.

While the use of a liner has been found to reduce static and sliding friction, those devices identified above which utilize such liners are still relatively complex in structure, manufacture, and operation and may be difficult to use effectively. In general their recommended usage requires the operator to hold, grip, or guide the penis during sheath application, a contact that is often considered objectionable and may not produce the desired results.

SUMMARY OF THE INVENTION

This invention is concerned broadly with a combination of an external male catheter and a tubular applicator which includes a continuous, friction-reducing sleeve that surrounds the applicator tube and is slideable along the outer and inner surfaces of the tube. While finger contact with the penis may be made at an initial stage in the application procedure to insure that the penis and the applicator are properly oriented with respect to each other, even such limited contact is seldom necessary. Later, during the actual application of the elastic sheath to the penis, both hands are in contact, not with the penis, but with the applicator tube and a portion of the sheath, one hand being used to grip and pull the outlet section of the sheath that projects through the open rear end of the applicator tube and the other hand being used to direct the applicator tube, maintaining its entrance opening in close proximity to the penis and, if desired, urging the sleeve and cylindrical body portion of the sheath towards that entrance opening.

The invention is particularly effective when used with an external catheter that has an inner sleeve 13 of the type disclosed in aforementioned U.S. Pat. No. 4,540,409, for reasons described in detail hereinafter. It is also desirable if the catheter sheath is of the adhesive-coated type, since the combination of this invention allows such a catheter to be applied to a patient with little or no risk that the pressure-sensitive adhesive coating of the sheath will be contacted by the user's fingers.

Briefly, the combination takes the form of an applicator tube supporting an external male urinary catheter with the distal portion of the catheter (which includes its outlet section) extending outwardly from one end of the tube and its cylindrical body section extending outwardly from the outer end of the tube and being everted about the outer surface of the tube. To reduce static and sliding friction between the tube and catheter, an endless, toroidally-shaped, mesh applicator sleeve is permanently and completely wrapped about the wall of the applicator tube for continuous rotational sliding movement thereabout. In operation, the outlet section of the sheath may be gripped directly between a user's fingers of one hand to pull the sheath from the rear end of the tube while the tube is being held and directed by the user's other hand. The pulling force exerted on the outlet section causes that portion of the sheath external to the rigid applicator tube to be reverted and pulled into and through the tube and, at the same time, causes the cylindrical body portion of the catheter to assume its final reverted position about the penile shaft.

The applicator of this invention is particularly advantageous as the applicator tube and continuous sleeve form a unitary part that eliminates many of the manufacturing and operating complications encountered with other more complex applicators, mentioned above, which have attempted to effectively use a liner to reduce static and sliding friction between an applicator tube and a catheter. Such a unitary applicator may be constructed in accordance with a method of this invention which includes the steps of inserting the sleeve through the tube and reverting the end portions of the sleeve about the outer surface of the tube so that the ends overlap. The ends of the sleeve are then permanently joined together with a heat seal so that the sleeve forms an endless torous which continuously surrounds the inner and outer surfaces of the tube without attachment thereto and is slideable and rotatable about the surfaces of the tube in somewhat the same manner as a tank tread travels about its supporting structure. To effectively produce such a construction, the sleeve is formed of a low-friction (preferably mesh) thermoplastic material that has a dissimilar heat-seal temperature than that of said applicator tube so that, when the ends of the sleeve are heat sealed together to form an endless toroidal belt, the ends will not be bonded to the tube and the structural integrity of the tube will not be affected by the heat. Once the unitary applicator is so formed, a catheter is inserted therethrough so that the outlet end projects through one end of the tube while the sheath is reverted about the other end of the sleeve-covered tube so that the cylindrical body portion is disposed about the outer surface of the tube, with the sleeve interposed therebetween, to form the applicator/catheter combination of this invention.

Since an adhesive-coated catheter is not supported in rolled condition upon the applicator tube, at least in the sense that inner and outer surfaces of the sheath are in direct concentric contact with each other, the outer surface of the sheath does not require a release coating of the type disclosed in prior patents such as U.S. Pat. No. Re. 33,206 and 4,581,026. A silicone release coating is typically applied to the outer surface of a conventional catheter while the release agent is in a dissolved state and the volatile solvents that have been commonly used in the past may present environmental concerns. Those concerns are eliminated by the combination of this invention because no such release coating is required.

Other features advantages, and objects of the invention will become apparent from the specification and drawings.

DRAWINGS

DETAILED DESCRIPTION OF PREFERRED EMBODIMENT

Figure 1:
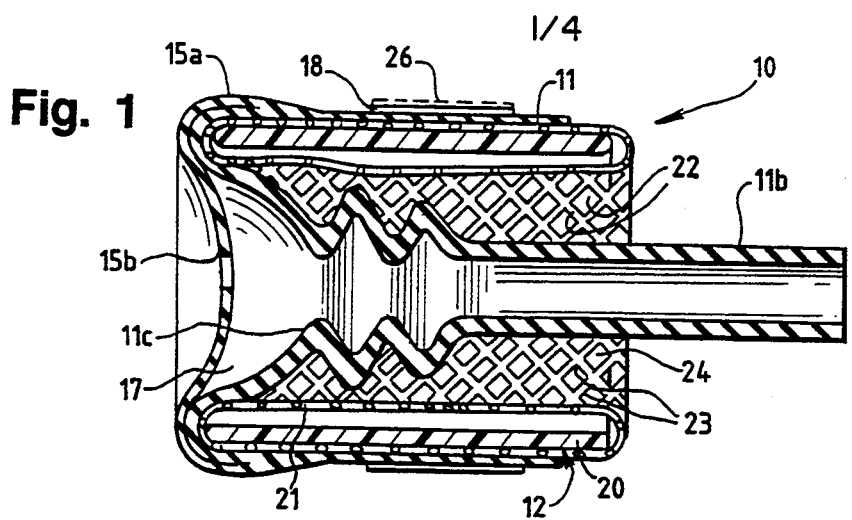
FIG. 1 is a longitudinal cross sectional view of a catheter and applicator combination constituting a preferred embodiment of this invention.

Referring to the drawings, the numeral 10 generally designates the combination of an external male catheter 11 and an applicator 12. The catheter may be an adaptation of a conventional external catheter of the type disclosed, four example, in U.S. Pat. Nos. 4,378,018 (FIG. 7) and 4,187,851 (FIG. 3); however, a catheter having the features disclosed in co-owned U.S. Pat. Nos. 4,581,026 and 4,540,409 is believed particularly desirable because of its inner sleeve construction and the presence of an internal band or zone of pressure-sensitive adhesive.

Figure 7:
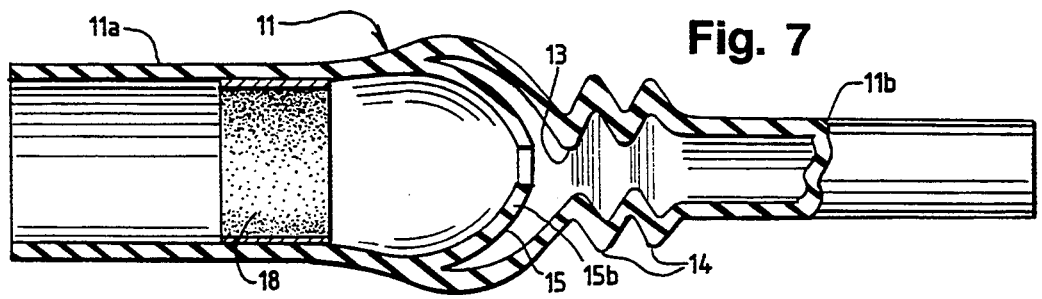
FIG. 7 is a longitudinal sectional view of a catheter which may be used with the applicator tube and continuous friction-reducing sleeve of this invention.

Catheter 11, shown most clearly in FIG. 7, is formed of soft, highly elastic, natural or synthetic rubber. Natural latex is preferred but other elastomers having similar properties, such as silicone rubber, may be used. The catheter comprises a sheath having an elongated cylindrical section 11a, a reduced outlet section 11b, and a tapered neck section 11c disposed therebetween. The wall thickness of the cylindrical section 11a is substantially less than that of the neck and outlet sections. For example the cylindrical section may have a wall thickness within the general range of 0.006 to 0.010 inches and, in general, is too thin or limp to retain a cylindrical configuration without support. In contrast, the wall thicknesses of the outlet and neck sections may be 0.050 inches or more and are generally great enough so that such sections will retain the configurations shown in the absence of distorting forces and will spring back into the illustrated shapes when distorting forces are removed.

At its forward or distal end, the neck section 11c is provided with a rounded taper leading to a reduced opening 13. The outlet section 11b that merges with the tapered neck section 11c is provided with a plurality of convolutions or annular enlargements 14. Two such convolutions of graduated size are depicted, their purpose being to permit greater stretchability, bending, and twisting of the outlet section when the device is in use, and to do so with less chance that kinking or obstruction of the lumen might occur. Also, since the interior of the outlet section is enlarged at such convolutions, the convolutions increase the fluid capacity of that section and, along with the neck section, provide a reservoir for accommodating surges of fluid when the catheter is in use.

In the particular embodiment illustrated, the catheter includes an inner sleeve section 15 with a proximal end portion 15a that merges smoothly with the distal end of the sheath's cylindrical body section 11a and an elongated distal end portion 15b disposed within the sheath's neck section 11c. The distal portion 15b tapers forwardly and inwardly, terminating in a reduced distal opening 16 that is spaced well behind (i.e., proximal to) opening 14. The setback also results in the provision of an annular and axially-elongated expansion space 17 between the outer surface of the sleeve's distal end portion 15b and the inner surface of neck section 11c. The wall thickness of the sleeve may be varied but, to insure conformability, good sealing properties, and wearer comfort, such thickness should approximate that of the relatively thin cylindrical body section 11a. Thus, both the cylindrical body section 11a and the inner sleeve 15 should appear as thin, limp, highly stretchable membranes, in contrast to the outlet and neck sections 11b and 11c with their shape-retaining properties.

In the preferred embodiment disclosed herein, the catheter or sheath 11 is also provided with an internal adhesive coating or band 18 (FIG. 7). The adhesive zone is located within the cylindrical section 11a of the sheath behind inner sleeve 15. While the adhesive coating might conceivably extend the full length of the cylindrical section 11a, it is believed preferable to provide the adhesive zone in the form of a narrow but continuous band located within the distal portion of the sheath's cylindrical section 11a. The adhesive coating may be composed of any suitable medical-grade pressure-sensitive adhesive of a type well known in the art; a hypoallergenic acrylic adhesive is believed to be particularly effective.

Applicator 12 comprises two components: a relatively rigid applicator tube 20 and a flexible, continuous, friction-reducing sleeve 21 in the form of endless torous that surrounds the wall of (and extends along the inner and outer surfaces of) the tube 20. Tube 20 is generally cylindrical in shape and is open at both its proximal and distal ends 20a and 20b, respectively. The edges of the tube at the proximal and distal ends 20a and 20b are preferably rounded (when viewed in longitudinal section). Tube 20 may be composed of any of a wide variety of generally stiff materials, a relatively rigid polyolefin such as polypropylene or high-density polyethylene being found particularly effective. Other polymeric materials, preferably thermoplastic, having similar properties may also be used.

Figure 3:
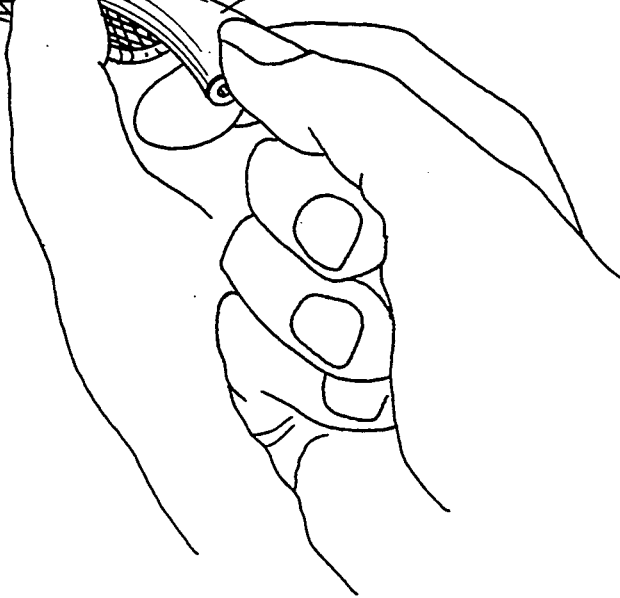
FIG. 3 is a perspective view of the catheter/applicator combination as it would be held by a user for application of a catheter to a patient.
Figure 4:
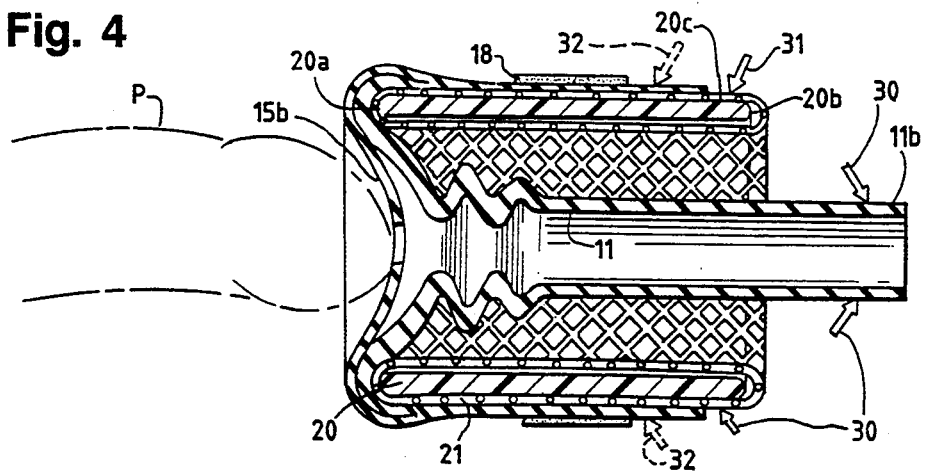
FIG. 4 is a longitudinal sectional view showing a first stage in the application of a catheter sheath.

The length of applicator tube 20 is substantially less than that of elastic sheath 11. The outside diameter of the applicator tube should be slightly greater than the maximum inside diameter of the sheath, particularly the cylindrical body section 11a thereof, in an unstretched state. Referring particularly to FIGS. 1 and 4, it will be observed that the length of the applicator tube is preferably greater than the length of the sheath's cylindrical body section 11a so that when the cylindrical body section is externally supported upon the outer surface of the applicator tube 20, an annular portion 20c of the tube's sleeve-covered outer surface adjacent distal end 20b is exposed and may be gripped (through sleeve 21) between the fingers during use of the device as depicted in FIG. 3.

The friction-reducing sleeve 21 is continuous and completely surrounds the inner and outer wall surfaces of tube 20. In the embodiment illustrated, the sleeve is composed of an open mesh of flexible, interconnected polymeric fibers or filaments. Two sets of such fibers 22 and 23 intersect to provide a multiplicity of mesh openings 24 with the parallel fibers of each set extending in directions that are not perpendicular to, and preferably not parallel with, the longitudinal axes of the applicator tube and sleeve. As a result, the sleeve may slide smoothly over the rounded edges at the proximal and distal ends 20a and 20b of tube 20 without a ratcheting action that might otherwise occur if the fibers of either set extended in a plane normal to the axis of the tube. Preferably, as shown in the illustrations given in FIGS. 2 and 3, mesh openings 24 have a greater length L (in a direction parallel to the longitudinal axis of the tube) than width W (in a radial direction) so that the sleeve has limited stretchability in the longitudinal direction but is more stretchable in the radial direction. The stretchability of the sleeve is limited in the longitudinal direction so that, during use, the sleeve does not stretch and impede application of the catheter, whereas the sleeve is more stretchable in the radial direction so that the sleeve can be stretched over the outer surface of the tube and a sleeve of specific diameter can be stretched over a range of tube sizes. The smooth fibers of the sleeve may be formed of any material that has a relatively low coefficient of friction with respect to the material of the applicator tube. A nylon (polyamide) mesh is believed suitable, and particularly effective results have been obtained utilizing a mesh formed of a polyolefin such as polypropylene or polyethylene. In particular, the frictional resistance between the sleeve 21 and the smooth surfaces of applicator tube 20 should be substantially less than the frictional resistance between the sleeve and the material of catheter sheath 11.

Figure 2:
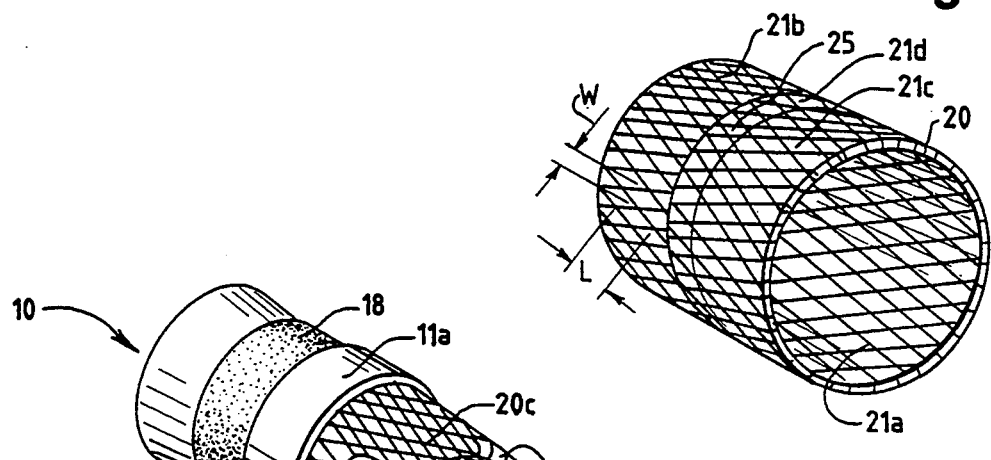
FIG. 2 is a perspective view of an applicator tube and a friction-reducing sleeve surrounding the tube in accordance with this invention.

FIG. 2 more clearly illustrates the positioning of sleeve 21 about tube 20. Sleeve 21 includes a first central portion 21a that extends along the inner surface of tube 20, but the central portion may also extend along the tube's other surfaces, depending upon the rotation of sleeve 21 about the wall of the tube. As shown, sleeve 21 is inserted through tube 20 with second and third end portions 21b and 21c extending outwardly through the respective ends of tube 20 and being reverted back onto the tube's outer surface to form an overlapping section 21d. Overlapping section 21d is heat sealed at 25 to join end portions 21b and 21c so that sleeve 21 continuously surrounds the wall of the open-ended tube 20 without attachment thereto. In such a construction, sleeve 21 loosely encases tube 20 so that it is slideable along the inner and outer surfaces of the tube to form a friction-reducing, slideable barrier between the tube and a catheter disposed thereon and extending therethrough. Preferably, sleeve 21 is constructed of a material that has a dissimilar heat seal temperature than that of tube 20 so that end portions 21b and 21c may be heat sealed together while the sleeve is in place upon the supporting tube 20 without affecting the structural integrity of that tube and without welding the sleeve to the tube. In constructions in which the tube has a lower heat seal temperature than that of the sleeve, the relatively thin sleeve ends are effectively heat sealed together in such a short period of time that the thicker tube wall is not effected by the heat and does not weld or otherwise bond to the sleeve. Such assembly of tube 20 and sleeve 21 together as a unitary applicator is particularly advantageous in that no further positioning of sleeve 21 is required when a catheter is disposed on the applicator.

FIG. 1 depicts the preferred catheter/applicator combination in a form in which it would be made available to users. The catheter sheath 11 has its neck and outlet sections extending axially within applicator tube 20 with outlet section 11b extending outwardly through distal end 20b of the applicator tube. The neck section 11c extends outwardly through the entrance opening at the tube's first or proximal end 20a and is reverted so that the cylindrical section 11a is disposed about the outside of the tube. The sheath does not, however, make direct contact with the tube due to the presence of the friction-reducing toroidal sleeve 21 which is wrapped about the wall of the tube.

If the cylindrical portion 11a of the sheath is provided with a band of pressure-sensitive adhesive 18, the adhesive is preferably covered by a release strip of siliconized paper or other material represented by phantom lines 26 in FIG. 1. The release strip would be peeled away by a user to expose the pressure-sensitive adhesive band before commencing the procedure of applying the sheath to a patient.

If the catheter sheath 11 is provided with an inner sleeve 15 as described and shown, then it has been found advantageous to mount the sheath upon tube 20 (with sleeve 21 interposed therebetween) so that the proximal end portion 15a of the sleeve 15 is also everted and is disposed about the outside of tube 20 adjacent the opening at the tube's proximal end 20a. The effect is to stretch or enlarge the proximal end of the sleeve and to reduce the length of that portion of the sleeve disposed within tube 20. Because the distal end portion 15b is thereby positioned at the entrance of the support tube 20, it is exposed in a manner that facilitates fitting the catheter upon a patient as described hereinafter.

FIG. 3 illustrates the catheter/applicator combination as it would be held by a user preparing to apply the catheter to a patient. The outlet section 11b of sheath 11 is firmly gripped between the fingers of one hand and the tube 20 is held between the fingers of the other hand. It has been found that the applicator tube 20 is most effectively supported if the user grips the exposed annular portion 20c near the distal end 20b of the tube through the open mesh construction of sleeve 21 in the manner illustrated. Alternatively, the applicator tube may be indirectly supported if the user grips a portion of the cylindrical section 11a of the sheath. The hand that supports the catheter/applicator combination (the left hand shown in FIG. 3) is used to orient the device so that the proximal end 20a of the tube is aligned with the penis and the glans engages the stretched sleeve portion 15b of the sheath (FIG. 4). The other hand (the right hand as shown in FIG. 3) exerts the force required for pulling the outlet section and catheter through the interior of tube 20 and, in so doing, everting the cylindrical section 11a of the sheath about the penile shaft of the patient while causing the low-friction mesh sleeve 21 to advance as an endless toroidal belt about the supporting tube 20. The hand that supports tube 20 through sleeve 21 may also be used to promote the sliding action between the sleeve and tube and which advances the sheath towards the tube's proximal end and facilitates application of the catheter.

It has been found that because of its smooth open-mesh construction, sleeve 21 slides easily with regard to applicator tube 20. At the same time, the openness of the mesh reduces the extent of surface contact between the sleeve and the outer and inner surfaces of the tube (and the rounded edges at the proximal and distal ends of the tube) to reduce the pulling force required for everting and applying the catheter.

Referring to FIG. 4, outlet section 11b is gripped and pulled by one hand in the directions indicated by arrows 30 while tube 20 is supported and advanced by the other hand in the directions represented by arrows 31. Gripping tube 20 through sleeve 21 allows the user to support the tube while also applying an axial force to the sleeve which advances the sleeve and the portion of the sheath disposed thereon towards end 20a and the penile shaft. However, as mentioned, the applicator tube may be indirectly supported and advanced by gripping the assembly as represented by dashed arrows 32 and, in that event, forward movement of the fingers towards the proximal end 20a of the tube also contributes to and promotes sliding action between the tube 20 on one hand and the sleeve 21 and catheter 11 on the other. In any event, a primary force causing the catheter to revert and unroll about the penis is the pulling force applied to the outlet section of the catheter and exerted in the direction of arrows 30.

Figure 5:
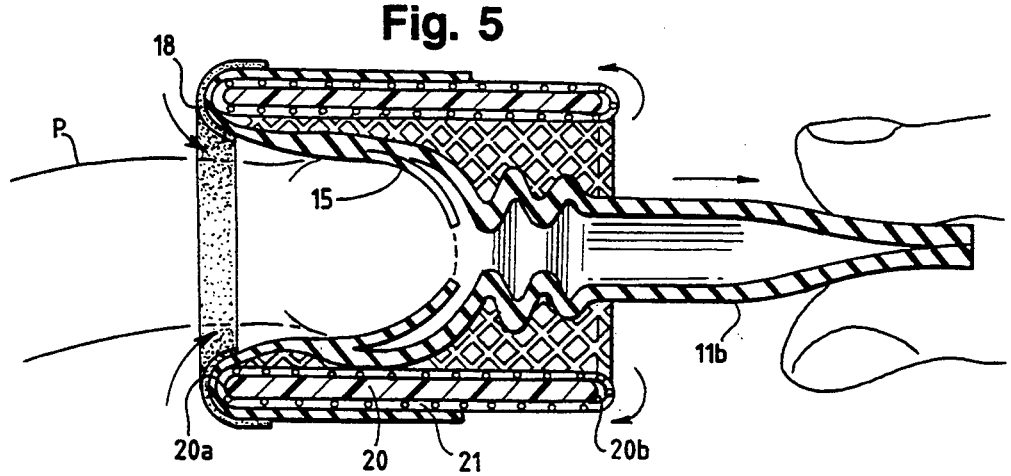
FIG. 5 illustrates an intermediate stage.
Figure 6:
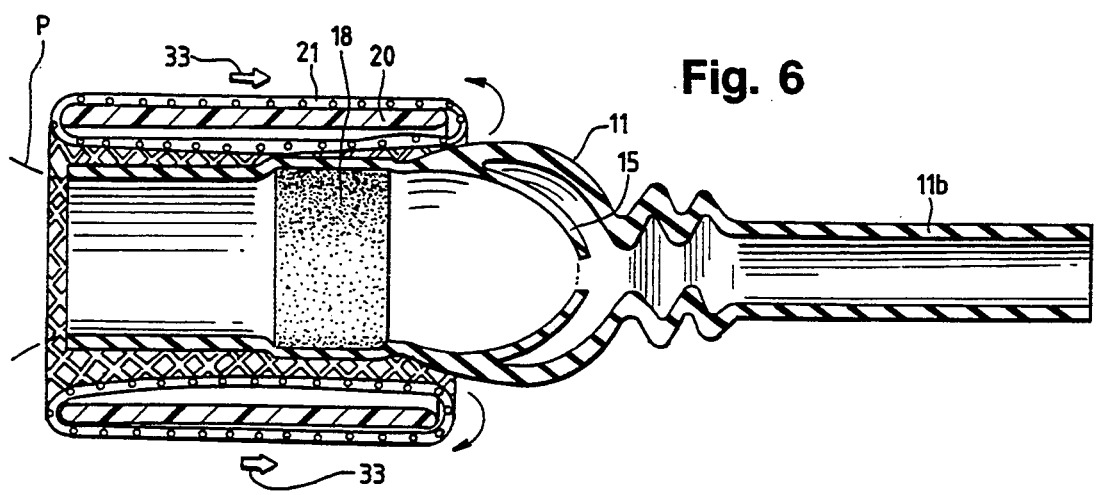
FIG. 6 depicts a final stage with the sheath fully applied.

FIG. 5 illustrates a further stage in the procedure of applying the catheter to a patient, the adhesive band 18 rolling about the rounded proximal edges of tube 20 for contact with the shaft of penis P. In FIG. 6, application of the catheter is complete, and all that remains is for the applicator tube 20 to be drawn away from the ensheathed penis in the direction represented by arrows 33.

While the applicator tube 20 of this invention may be used with a catheter that lacks inner sleeve 15, particularly effective results are achieved with a catheter having such an inner sleeve. The reason is that the stretched distal portion 15b of the inner sleeve may be brought into direct contact with the end of the penis in the first step of applying the sheath (FIG. 4) and then, as the sheath is reverted and applied, inner sleeve 15 is pulled and stretched tightly over the glans to form a non-adhesive liquid-tight seal (FIGS. 5 and 6). That seal is then maintained, with the inner sleeve 15 in stretched condition, because of the adhesive contact between band 18 and the penile shaft in an area well behind the glans. In cases where the inner sleeve 15 is omitted, it may be considered necessary or desirable to commence the reverting action without first bringing the sheath into direct contact with the glans because such contact with the relatively thick tapered neck section 11c of the catheter sheath may be undesirable in terms of patient comfort and the elimination of space that would otherwise function as a surge chamber.

Figure 8:
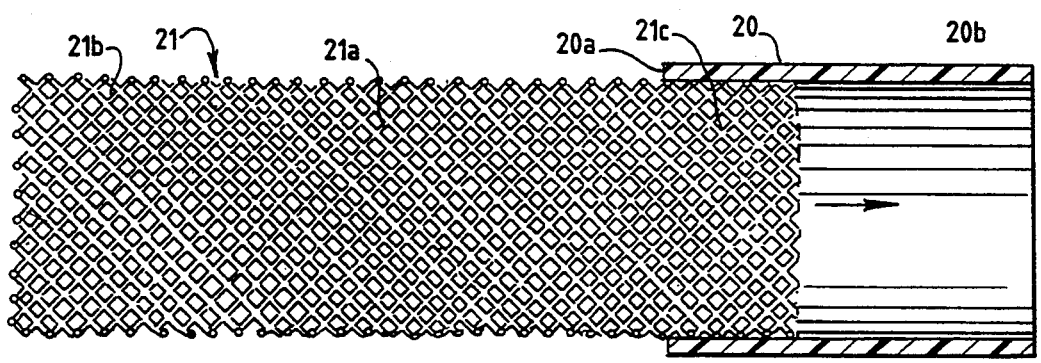
FIG. 8 is a side, schematic, cross-sectional view showing a first step in making the applicator of this invention.
Figure 9:
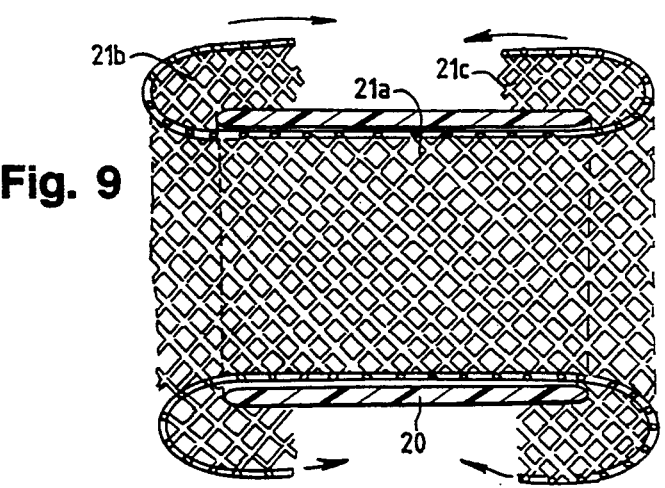
FIG. 9 is a side, schematic, cross-sectional view illustrating a second step of making the applicator.
Figure 10:
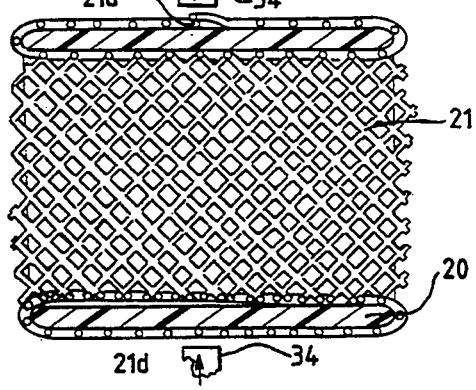
FIG. 10 is a side, schematic, cross-sectional view illustrating another step in the process of making the applicator.
Figure 11:
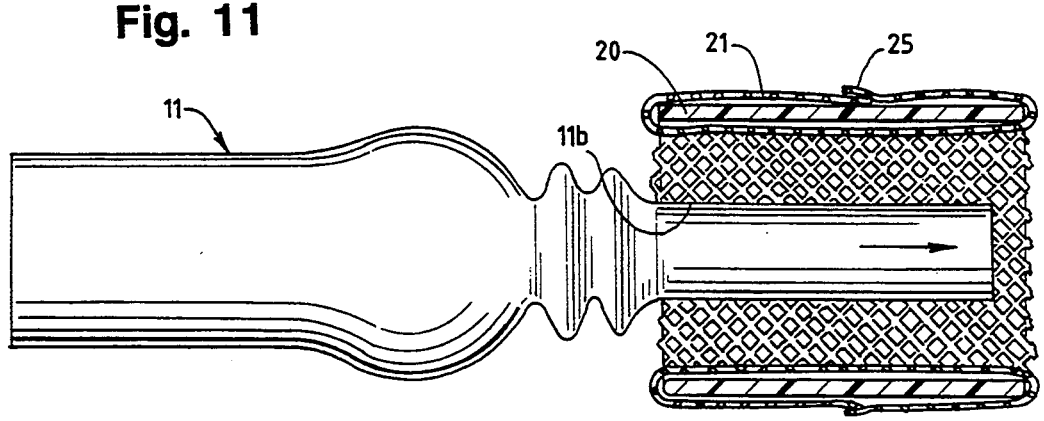
FIG. 11 is a side, schematic, partial cross-sectional view showing a further step in making the catheter/applicator combination of this invention.
Figure 12:
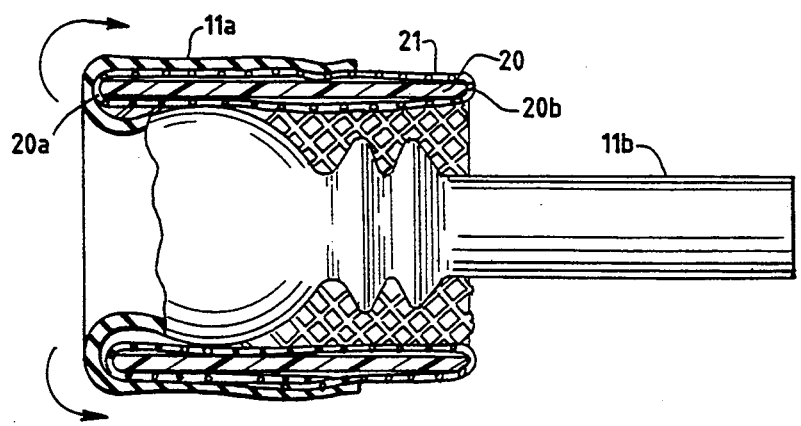
FIG. 12 is a side, schematic, partial cross-sectional view showing another step of making the catheter/applicator combination.
Figure 13:
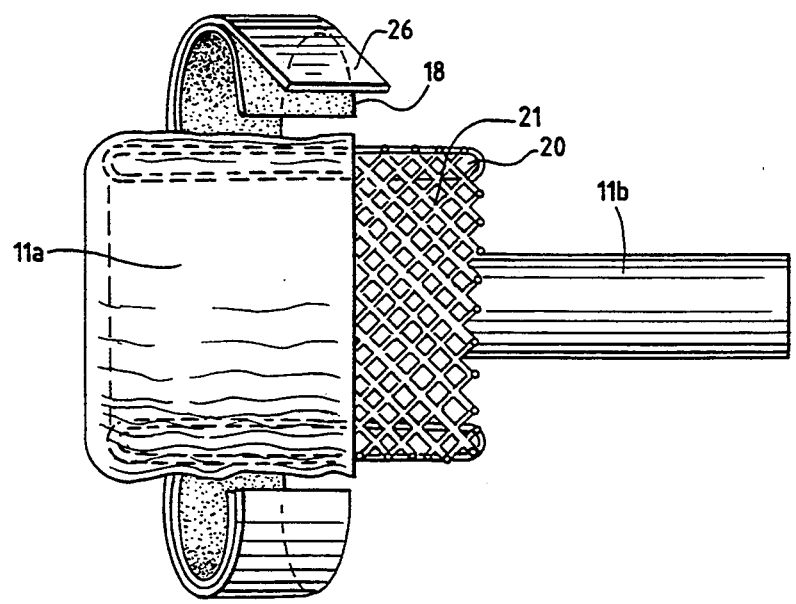
FIG. 13 is a schematic, side view showing a further step of adding an adhesive strip to the catheter/applicator combination.

FIGS. 8–13 illustrate a preferred method of making the applicator and catheter/applicator combination of this invention. In FIG. 8, tube 20 is firmly supported by clamping or other means, and tubular sleeve 21 is inserted through the tube until central portion 21a of sleeve 21 extends along the inner surface of the tube. Second and third end portions 21b and 21c of sleeve 21 are then reverted about tube ends 20a and 20b as shown in FIG. 9 until the end portions extend along the outer surface of the tube and overlap at section 21d, as illustrated in FIG. 10. A die stamp, schematically shown at 34, is then used to heat seal end portions 21b and 21c together at overlapping section 21d so that sleeve 21 continuously surrounds tube 20 without bonding thereto and is slideable along the inner and outer surfaces of the tube. For that purpose, sleeve 21 is constructed of a thermoplastic material that has a dissimilar heat-seal temperature than that of tube 20 so that end portions 21b and 21c may be heat-sealed together about tube 20, using the rigid tube as a supporting mandrel, without affecting the structural integrity of the tube or causing the sleeve to become heat-sealed or welded to the tube. In constructions in which the tube has a lower heat seal temperature than that of the sleeve, the heat seal temperature is applied to the relatively thin sleeve ends for such a short period of time that the thicker tube wall is not effected and does not weld or otherwise bond to the sleeve. Once tube 20 and sleeve 21 are assembled as a unitary applicator, sheath 11 is inserted through tube 20 (FIG. 11) until outlet section 11b extends through second end opening 20b (FIG. 12). Sheath 11 in then reverted about first end 20a so that cylindrical body portion 11a is disposed about the outer surface of tube 20 with sleeve 21 being interposed therebetween (FIG. 12). Adhesive band 18 is then applied, preferably, by using a tape transfer means wherein release layer 26 and adhesive layer 18 are wrapped around the outer most surface of cylindrical body portion 11a. Release layer 26, which has less affinity for the adhesive than the elastomeric material of the catheter, may then be removed prior to application of the catheter.

While in the foregoing, embodiments of the invention have been disclosed in considerable detail for purposes of illustration, it will be understood by those skilled in the art that many of these details may be varied without departing from the spirit and scope of the invention.

I claim:

1. An applicator for applying an external male catheter, said applicator comprising a relatively rigid tube having a wall defining inner and outer surfaces and having oppositely-facing first and second end openings; and a flexible, tubular sleeve having a first portion extending along one of said outer and inner surfaces of said tube and having second and third end portions being reverted onto the other of said outer and inner surfaces of said tube, said second and third end portions being joined together so that said sleeve constitutes an endless toroidal belt that continuously surrounds the wall of said tube without being bonded thereto and is rotatably slideable along and about said inner and outer surfaces of said tube.

2. The applicator of claim 1 in which said sleeve and tube are formed of thermoplastic materials with the material of said sleeve having a dissimilar heat-seal temperature than that of said applicator tube.

3. The applicator of claim 1 in which said sleeve comprises a continuous mesh of intersecting, essentially non-stretchable, polymeric filaments.

4. The applicator of claim 3 in which said filaments of said mesh sleeve comprise two sets of spaced parallel filaments with the filaments of each set extending in directions that are not parallel with or perpendicular to a plane normal to the axis of said applicator tube.

5. The applicator of claim 4 in which said filaments are composed of a polyolefin which has a dissimilar heat-seal temperature than that of said applicator tube.

6. An external catheter and applicator combination, said catheter comprising a sheath of thin, stretchable, elastic material having a generally cylindrical body section merging at one end with a tapered neck section terminating in an outlet section of reduced diameter; said applicator including a relatively rigid tube having inner and outer surfaces and having oppositely-facing first and second end openings; said tube having a length substantially less than that of said sheath and having an outside diameter slightly greater than the maximum inside diameter of said sheath in an unstretched state; said applicator also including a flexible, tubular sleeve having a first portion extending along one of said outer and inner surfaces of said tube and having second and third end portions being reverted onto the other of said outer and inner surfaces of said tube, said second and third end portions being joined together so that said sleeve constitutes an endless toroidal belt that continuously surrounds the wall of said tube without being bonded thereto and is rotatably slideable along and about the outer and inner surfaces of said tube; said sheath having its neck and outlet sections extending axially within said applicator tube with at least a portion of its outlet section extending through the second end of the applicator tube; said sheath extending outwardly through said first end opening and being reverted so that said cylindrical body section is disposed about the outer surface of said tube with said sleeve being interposed therebetween; the frictional resistance between said sleeve and said tube being substantially less than the frictional resistance between said sleeve and said sheath; whereby, said sheath may be applied to a patient by positioning said tube's first end opening at the glans of a penis and then pulling said outlet section of the sheath away from said tube to extract said sheath from the interior of said tube and simultaneously evert and advance the sheath's cylindrical body section onto the penile shaft.

7. The combination of claim 6 in which said tube is cylindrical.

8. The combination of claim 6 in which said tube is longer than said cylindrical body section of said sheath.

9. The combination of claims 6, 7 or 8 in which said cylindrical body section of said sheath extending about said outer surface of said tube has an outwardly facing surface; at least a portion of said outwardly facing surface having a pressure-sensitive adhesive coating thereon.

10. The combination of claims 6, 7 or 8 in which said sheath also includes an inner sleeve section disposed within said neck section and exposed at said first end opening of said tube.

11. The combination of claim 6 in which said sleeve and tube are formed of thermoplastic materials with the material of said sleeve having a dissimilar heat-seal temperature than that of said applicator tube.

12. The combination of claim 6 in which said sleeve comprises a continuous mesh of intersecting, essentially non-stretchable, polymeric filaments.

13. The combination of claim 12 in which said filaments of said mesh sleeve comprise two sets of spaced parallel filaments with the filaments of each set extending in directions that are not parallel with or perpendicular to a plane normal to the axis of said applicator tube.

14. The combination of claim 13 in which said filaments are composed of a polyolefin which has a dissimilar heat-seal temperature than that of said applicator tube.

15. A method of applying an external male catheter to the penis of a patient, said catheter comprising a sheath of thin, stretchable, elastic material having a generally cylindrical body section merging at one end with a tapered neck section terminating in an outlet section of reduced diameter; said sheath being supported by a relatively rigid open-ended applicator tube wherein said sheath has its neck and outlet sections axially disposed within said tube and said sheath projects outwardly from one end of said tube where it reverses direction so that said cylindrical body section is everted and disposed externally of said tube, said outlet section of said sheath extending from a second end of said tube; and a friction-reducing continuous sleeve surrounding said tube and being interposed between said tube and said sheath, said sleeve being in the form of an endless toroidal belt: that extends continuously about the wall of said tube and is slideable along said outer and inner surfaces of said tube for rotation of said sleeve about said wall; said method comprising the steps of introducing the glans of a penis into the neck section of said sheath at said one end of said tube; then gripping said outlet section of said sheath to extract said sheath from said opposite end of said tube while at the same time urging said tube towards the penis, and rotating said sleeve about the wall of said tube for everting said cylindrical body section of said sheath and directing the same onto the penis.

16. The method of claim 15 in which said sheath also includes an inner sleeve section disposed within said neck section and spaced from the inner surface thereof; said step of introducing the glans of the penis into the neck section including the step of urging said sleeve section into direct contact with the glans.

* * * * *